United States Patent [19]

Varadaraj et al.

[11] Patent Number: 5,571,715
[45] Date of Patent: Nov. 5, 1996

[54] SURFACE ACTIVE METAL CHELATED NUTRIENTS FOR BIOREMEDIATION OF HYDROCARBON CONTAMINATED SOILS AND WATER

[75] Inventors: Ramesh Varadaraj, Flemington; Stanley J. Brois, Westfield; Jan Bock, Warren; Cornelius H. Brons, Washington, all of N.J.

[73] Assignee: Exxon Research and Engineering Company, Florsham Park, N.J.

[21] Appl. No.: 375,748

[22] Filed: Jan. 20, 1995

[51] Int. Cl.$^6$ .................................................. C12N 1/38
[52] U.S. Cl. .................... 435/244; 210/610; 210/631; 210/925; 252/344; 252/352; 252/357; 435/248; 435/262.5; 435/281
[58] Field of Search .................... 210/610, 611, 210/631, 747, 922, 925; 252/341, 344, 352, 357, DIG. 11; 435/243, 244, 248, 281, 262.5

[56] References Cited

U.S. PATENT DOCUMENTS

| | | | |
|---|---|---|---|
| 4,243,549 | 1/1981 | Messenger et al. | 252/355 |
| 4,414,333 | 11/1983 | Olivieri et al. | 210/922 |
| 4,569,750 | 2/1986 | Brownawell et al. | 585/950 |
| 4,966,997 | 10/1990 | Shanzer et al. | 435/244 |
| 5,300,227 | 4/1994 | Varadaraj et al. | 210/925 |
| 5,436,160 | 7/1995 | Varadaraj et al. | 435/281 |

*Primary Examiner*—Peter A. Hruskoci
*Attorney, Agent, or Firm*—Joseph J. Dvorak

[57] ABSTRACT

The present invention provides for enhanced bioremediation of hydrocarbon contaminated soils and waters by treating soil or water with a composition comprising of a metal chelated macrocyclic amido amines or mixtures thereof represented by the structural formula:

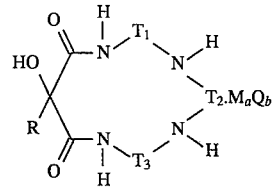

where R is selected from linear or branched alkanes with 8 to 22 carbons, linear or branched alkenes with 4 to 22 carbon atoms;

$T_1$, $T_2$ and $T_3$ are independently selected from ethylene, trimethylene, $CH_2CH_2(NHCH_2CH_2)_x$ where x is an integer from 1 to 10;

$M_aQ_b$ is a metal compound wherein M is a cation selected from cations of Fe, Co, Ni, Cu, Zn, and Mn; and, Q is an anion selected from nitrate, phosphate anions; and a and b are integers from 1 to 3 necessary to satisfy the valence requirements of M and Q.

a phosphorous source, and a diluent.

5 Claims, 1 Drawing Sheet

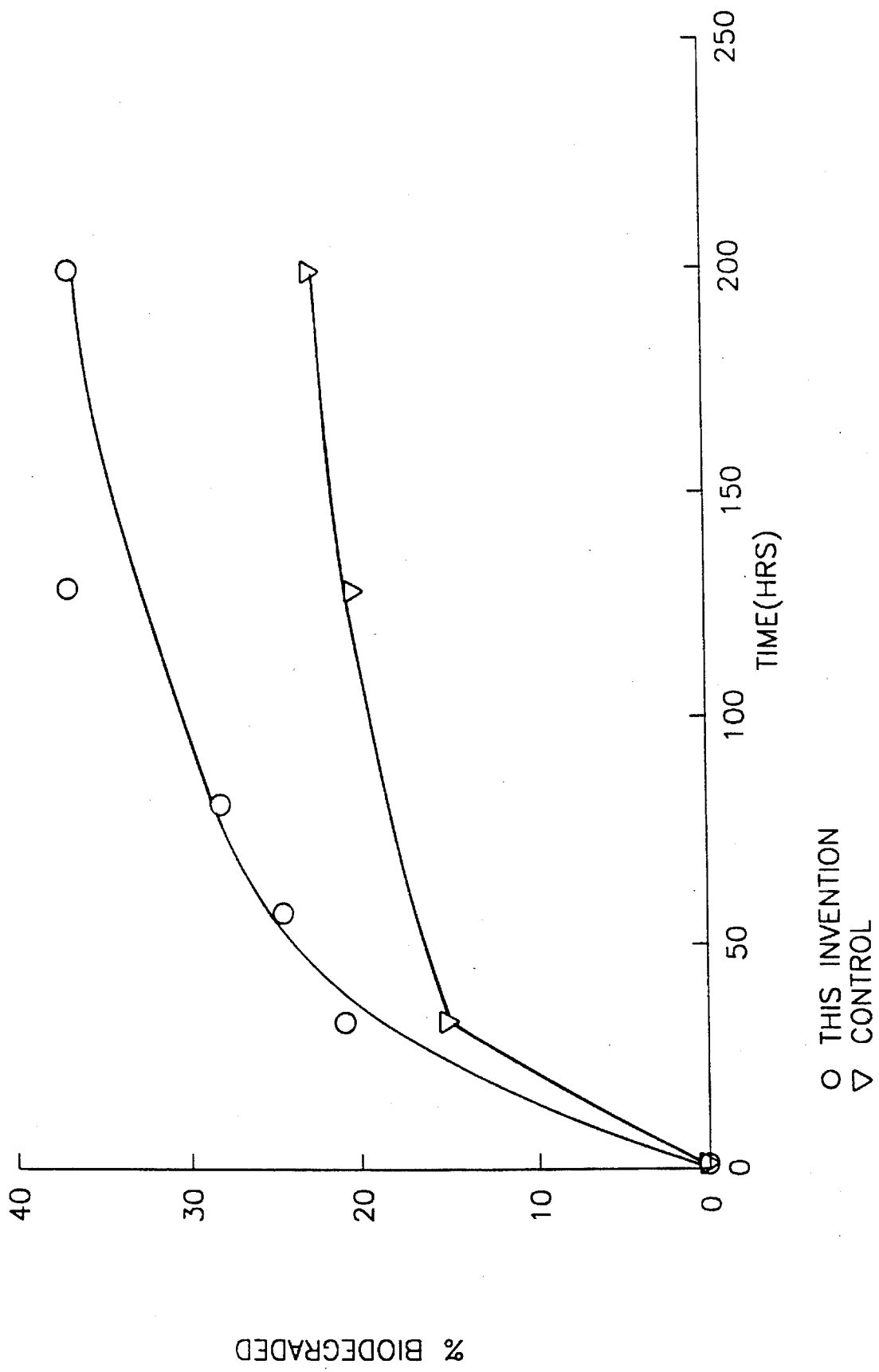

SURFACE ACTIVE METAL CHELATED NUTRIENTS FOR BIOREMEDIATION OF HYDROCARBON CONTAMINATED SOILS AND WATER

FIELD OF INVENTION

This invention relates to surface active chelated nutrient compounds suitable for enhancing the microbiological degradation of hydrocarbons in soils and water.

BACKGROUND OF THE INVENTION

It is well known that there are several microbial species found in soil and water that are capable of assimilating petroleum hydrocarbons. Unfortunately, the rate of microbial assimilation of petroleum hydrocarbons is relatively slow. It is necessary, therefore, to enhance the biological process if bioremediation is to be applied as a practical soil and water decontamination process.

In general, the rate and extent of microbial utilization of petroleum hydrocarbons is limited by the concentration of microbial nutrients and microflora available at the hydrocarbon-water interface. Thus, microbial nutrients, especially nitrogen containing nutrients like urea and ammonium nitrate have been added to contaminated soil or water as a method for enhancing the biodegradation of the hydrocarbon contaminants. Because these nitrogen containing microbial nutrients are generally water soluble and because the petroleum hydrocarbons are hydrophobic, the nutrients are generally delivered in an aqueous solution, along with a surface active agent which makes the contaminant bio-available to the hydrocarbon degrading microbes.

Notwithstanding the benefits resulting from using aqueous solutions of microbial nutrients, trace metals like Fe, Cu, Ni, Zn, Co and Mn are also useful as additional microbial nutrients. These metals are typically delivered in aqueous solution, often in the form of a complex with ethylene diamine tetraacetic acid (EDTA). Although this approach is useful, there remains a need for better approaches to making microbial nutrients and trace metals bio-available to the microbes at the hydrocarbon contaminant-water interface.

One object of the present invention therefore is to enhance the bioavailability of microbial nutrients by providing molecules that are surface active and have nutrient attributes.

Another object of the present invention is to provide a composition and method for stimulating the propagation of naturally occurring hydrocarbon assimilating microflora to enhance the bioremediation of hydrocarbon contaminated water and soils.

SUMMARY OF THE INVENTION

In one embodiment, the present invention comprises treating a hydrocarbon contaminated soil or water with a compound capable of reducing the interfacial tension between water and the hydrocarbon contaminant and selected from the group consisting of metal chelated macrocyclic amido amines. In another embodiment of the present invention there is provided a composition useful in treating hydrocarbon contaminated soil or water comprising:

a compound selected from the group consisting of metal chelated macrocyclic amido amines and mixtures thereof, a phosphorous source; and a liquid diluent.

These and other embodiments of the invention will be described in detail hereinafter.

BRIEF DESCRIPTION OF THE DRAWING

The accompanying FIGURE graphically compares the amount of hydrocarbon degraded over time in a test using a composition of this invention and a control.

DESCRIPTION OF THE PREFERRED EMBODIMENTS

The present invention provides for enhanced bioremediation of hydrocarbon contaminated soils and waters by treating the soil or water with a microbial assimilable surface active nutrient compound selected from the group consisting of metal chelated macrocyclic amido amines and mixtures thereof.

The preferred metal chelated macrocyclic amido amines are represented by the structural formula:

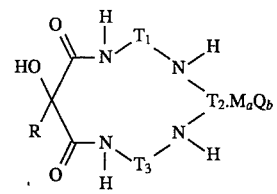

where R is selected from linear or branched alkanes with 8 to 22 carbons, linear or branched alkenes with 4 to 22 carbons;

$T_1$, $T_2$ and $T_3$ are independently selected from ethylene, trimethylene, $CH_2CH_2(CH_2CH_2)_x$ where x is an integer from 1 to 10;

$M_aQ_b$ is a metal compound wherein M is a cation selected from cations of Fe, Co, Ni, Cu, Zn, and Mn; and Q is an anion selected from nitrate, phosphate; and a and b are integers from 1 to 3 necessary to satisfy the valence requirements of M and Q.

The metal chelated macrocyclic amido amines suitable in the present invention are readily prepared by adding a metal salt to a macrocyclic amido amine. Macrocyclic amido amines in turn are prepared by condensing polyamines with ene and radical adducts of vicinyl tricarbonyl compounds. Each of these steps will be described in detail hereinafter.

First, ene adducts useful in the present invention are prepared by contacting an unsaturated hydrocarbon having from 8 to 22 carbon atoms with a vicinyl tricarbonyl compound, especially a cyclic vicinyl tricarbonyl such as pyrimidine trione at a temperature at which thermal ene addition occurs without appreciable decomposition. This, of course, is possible because of the high reactivity of pyrimidine tetrone. Generally, reaction temperatures within the range of from about 20° C. to about 200° C. are useful. The reaction temperature will vary depending upon the particular unsaturated hydrocarbons that are employed. Effective contacting of the olefin and tricarbonyl can be achieved by combining these reactants together with a solvent, or neat. The contacting is continued for a time sufficient to form the adduct.

Radical adducts of vicinyl tricarbonyl such as pyrimidine trione are prepared by contacting an aliphatic hydrocarbon with the carbonyl in the presence of a free radical initiator. Radical grafting of hydrocarbons is conveniently conducted without a solvent or diluent. For example, a neat hydrocarbon such as pristane, and about 2 wt. % (based on hydrocarbon weight) of pyrimidine tetrone are combined in a nitrogen-blanketed reactor, at about 160° C. Radical grafting is initiated by adding in one dose, about 1–100 wt. % (based on monomer weight) of a free radical initiator such as t-butyl peroxide for example, and stirring the mixture at 160° C. until radical grafting is complete.

Next, the foregoing ene and radical adducts connected to the macrocyclic imido amines are condensed with polyamines such as 3,3'-amino-bis-propylamine, diethylenetriamine, triethylene tetraamine, 1,3-bis-(2-aminoethyl) -1,3 propanediamine, tetraethylenepentamine and polyamine-H ( a mixture of higher ethylene amines including pentaethylene-hexamine). The condensation is conducted in a solvent such as dioxane at a temperature in the range of from about 25° C. to about 100° G., and preferably at about 60° C. for several hours, e.g., about 5 to 8 hours.

Addition of molar equivalents of a metal salt to a macrocyclic amido amine affords the corresponding metal chelated macrocyclic amido amine. Chelation can be readily carried out by combining the reactants together neat or in a solvent.

An important aspect of the present invention is the fact that the described metal chelated macrocyclic amido amines speed up the natural process of biological degradation by performing two functions: (1) increasing the interface between the hydrocarbon contaminant in the soil or water, the microflora and nutrients and (2) propagation of the microflora by supplying microbial nutrients and trace metals at the interface.

Specific illustrative examples of metal chelated macrocyclic amido amines having the formula below are given in Table 1

TABLE 1

| Compound | Formula |
|---|---|
| 1. | $T_1 = T_3$ = ethylene<br>$T_2$ = trimethylene<br>R = 2-Octadecenyl<br>M = Fe<br>Q = $NO_3$<br>a = 1, b = 3 |
| 2. | As above in 1 but with<br>Q = $PO_4$<br>a = b = 1 |
| 3. | As above in 1 but with<br>M = Cu<br>Q = $NO_3$<br>a = 1, b = 2 |
| 4. | $T_1 = T_2 = T_3$ = ethylene<br>R = 2-Octadecenyl<br>M = Co<br>Q = $NO_3$<br>a = 1, b = 2 |

Key interfacial properties of some of these surface active metal chelated macrocyclic amido amines are given in Table 2.

TABLE 2

| Composition (Compound of TABLE 1) | 1 | 2 | 3 |
|---|---|---|---|
| Interfacial property at 25°C.<br>Air-Water Interface[1] | | | |
| Critical micelle concentration, CMC (M) | $8.7 \times 10^{-4}$ | $1.0 \times 10^{-3}$ | $2.5 \times 10^{-3}$ |
| Surface tension at CMC (dynes/cm) | 48.0 | 32.5 | 49.5 |

TABLE 2-continued

| Composition (Compound of TABLE 1) | 1 | 2 | 3 |
|---|---|---|---|
| Hydrocarbon-Water Interface[2] | | | |
| Interfacial tension against cyclohexane (dynes/cm) | 14.0 | 30.7 | 27.1 |
| Interfacial tension against toluene (dyes/cm)<br>Paraffin-Water Interface[3]<br>Contact Angle | 11.0 | 18.1 | 8.5 |
| Advancing (degrees) | 88 | 72 | 90 |
| Receding (degrees) | 68 | 23 | 62 |

1. Air-water interfacial properties determined using the Wilhelmy plate method.
2. Hydrocarbon-water interfacial tension determined by the pendant drop method.
3. Parafilm-water contact angle determined by the dynamic contact angle method using a Cahn balance DCA analyzer.

In treating hydrocarbon contaminated soil or water with the metal chelated macrocyclic amido amine it is preferred to deliver them by broadcasting, spraying or the like, dispersed or dissolved in a solvent. Water is the preferred solvent for those metals chelated amido amine compounds that are water soluble.

In those instances when the metal chelated macrocyclic imido amine is water dispersible a co-solvent may be employed. Suitable co-solvents include alcohols such as isopropyl alcohol.

When the metal chelated macrocyclic imido amine is water insoluble, they can be delivered to the contaminated soil or water as a solution in a hydrocarbon solvent. Easily biodegradable low molecular weight petroleum distillates having a high normal paraffin content such as Norpar® solvents sold by Exxon Company USA, Houston, Tex., are especially preferred hydrocarbon solvents.

The metal chelated macrocyclic compounds of the present invention can provide the nitrogen and phosphorous requirements for microbial growth by using mixtures of metal nitrate and metal phosphate chelates, however, other phosphorus sources such as, ammonium phosphate, trilaureth phosphate and alkyl phosphates can also be used in conjunction with the metal chelated macrocyclic amido amines of the present invention to provide the desired balance of nutrients. Similarly, mixtures of different metal chelated macrocyclic amido amines can provide an appropriate spectrum of trace metals for microbial utilization. In general, mixtures of the metal chelated macrocyclic compounds or the metal chelated macrocyclic compound and phosphorous source are combined to provide a N:P weight ratio of about 10:1 to about 10:5. Additionally, the metal chelated macrocyclic compounds of the present invention may be combined with a co-surfactant such as nonionic, anionic or cationic surfactants to provide added surfactancy, if desired.

Thus the present invention provides a composition useful in treating hydrocarbon contaminated soil and water comprising a chelated macrocyclic compound of the current invention, a phosphorous source, cosurfactants and a diluent.

A preferred composition will contain from 20% to about 80% by weight of the macrocyclic compound and phosphorous source based on the total weight of the composition with the balance being co-surfactant if any and diluent.

The foregoing compositions are applied to soil or water at the rate of 5 wt. % to 30 wt. % of treat to hydrocarbon contaminant. The amount of treat is added to achieve a C:N:P ratio in the range 100:10:1 to 100:1:0.1 the preferred range being 100:2:0.2.

EXAMPLE

The biodegradation of an Alaskan North Slope Crude oil 520°–1050° F. distillate cut was tested with a composition comprising of:
(a) 66 wt. % Compound 1 of Table 1 as the nitrogen source
(b) 24 wt. % of trilaureth phosphate as the phosphorous source.
(c) 20 wt% water as diluent For these tests, 10 wt. % of the composition to oil was used. The C:N:P ratio was 100:1:0.1

For comparative purposes, a control was run with no addition of nutrients (Control). The tests were conducted as follows:

Shake flask cultures for assay of the biological efficacy were set up in sterile 300 ml baffled flasks. Each flask contained 135 ml of a sterile mineral medium with 0.5 g of hydrocarbon added. The chelated macrocyclic amido amine formulation was first thoroughly mixed with the hydrocarbon before the mixture was added to the culture flask. Flasks were incubated at 25° C. Aeration was achieved by shaking at 125 rpm. Inoculation for biological activity was made at 10%, e.g., 10 ml of inoculum per 100 ml culture.

Inoculum for biological activity was provided using clarified sludge from process water biological oxidation unit of a commercial petroleum refinery. The inoculum was prepared by stirring approximately 900 ml of the sludge with aeration. After 24 hours, the aerated sludge was centrifuged and the pellet re-suspended in the mineral medium to generate the inoculum.

The percentage of hydrocarbon biodegraded was determined by gas chromatography after 32, 56, 80, 128 and 200 hrs. of experiment. Results are graphically illustrated in the FIGURE.

What is claimed is:
1. A composition comprising:
a compound selected from the group consisting of metal chelated macrocyclic amido amines, and mixtures thereof represented by the formula:

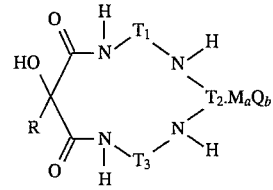

wherein R is selected from linear and branched alkanes of from about 8 to about 22 carbon atoms, linear and branched alkenes having from about 4 to about 22 carbon atoms; $T_1$, and $T_2$ and $T_3$ are independently selected from ethylene, trimethylene, $CH_2CH_2(NHCH2CH2)_x$; x is an integer of from 1 to 10; $M_aQ_b$ is a metal compound wherein M is a cation selected from Fe, Co, Ni, Cu, Zn and Mn cations; Q is an anion selected from nitrate, phosphate; and a and b are integers from 1 to 3 necessary to satisfy the valence requirements of M and Q; a phosphorous source; and, a diluent and wherein the metal chelated macrocyclic amido amine and the phosphorous source are combined to provide a N:P ratio of from about 10:1 to 10:5.

2. The composition of claim 2 wherein the phosphorous source is selected from ammonium phosphate, trilaureth phosphate and alkylphosphates having 8 to 22 carbon atoms in the alkyl group and mixtures thereof.

3. The composition of claim 2 wherein the diluent is selected form the group consisting of water, low molecular weight hydrocarbons, and water-alcohol mixtures.

4. The composition of claim 3 including a co-surfactant selected from nonionic, anionic and cationic surfactants.

5. The composition of claim 4 wherein the macrocyclic compound and phosphorous source are present in an amount ranging from about 20% to about 80% by weight of the total weight of the composition.

* * * * *